United States Patent [19]

Georgi

[11] Patent Number: 5,509,303
[45] Date of Patent: Apr. 23, 1996

[54] CONTROLLABLE SENSITIVITY DIFFERENTIAL PRESSURE FLUID DENSITY INSTRUMENT

[75] Inventor: Daniel T. Georgi, Houston, Tex.

[73] Assignee: Western Atlas International, Inc., Houston, Tex.

[21] Appl. No.: 386,948

[22] Filed: Feb. 10, 1995

Related U.S. Application Data

[63] Continuation-in-part of Ser. No. 359,581, Dec. 20, 1994.

[51] Int. Cl.$^6$ .............................. G01N 9/26; E21B 47/00
[52] U.S. Cl. .............................................. 73/151; 73/438
[58] Field of Search .......................... 73/151, 155, 438, 73/32 R

[56] References Cited

U.S. PATENT DOCUMENTS

| | | | |
|---|---|---|---|
| 2,747,401 | 5/1956 | Doll | 73/151 |
| 3,184,965 | 5/1965 | Noik | 73/438 |
| 3,455,157 | 7/1969 | Lahaye et al. | 73/438 |
| 3,616,688 | 11/1971 | Roussin et al. | 73/151 |

*Primary Examiner*—Michael J. Brock
*Attorney, Agent, or Firm*—Richard A. Fagin

[57] ABSTRACT

The present invention is a differential pressure fluid density instrument comprising a housing having a plurality of ports positioned at spaced-apart locations along the housing, a differential pressure transducer, and a valve adapted to selectively connect the transducer across two predetermined one of the plurality of ports. The valve may comprise a three-way solenoid actuated valve. Fluid expansion wells are each connected at one end to a port and prevent wellbore fluids from reaching the differential pressure transducer. The housing includes an inner chamber filled with liquid which may be silicon oil. The chamber includes a standpipe which extends from near the bottom of the chamber, where it is in communication with a lower port, to the top of the chamber. Communication between the chamber and wellbore through the standpipe enables the housing and components disposed within the chamber to be constructed without the need to withstand high differential pressures.

5 Claims, 2 Drawing Sheets

CONTROLLABLE SENSITIVITY DIFFERENTIAL PRESSURE FLUID DENSITY INSTRUMENT

CROSS REFERENCE TO RELATED APPLICATIONS

The present application is a continuation-in-part of U.S. patent application Ser. No. 08/359,581 filed on Dec. 20, 1994 and assigned to the assignee of the present invention.

BACKGROUND OF THE INVENTION

1. Field of the Invention

The present invention relates to the field of wellbore production logging tools. More specifically, the present invention relates to a tool for measuring the density of a fluid filling a wellbore by means of measuring a differential pressure between two spaced-apart locations along the tool.

2. Discussion of the Related Art

Production logging tools are used in wellbores penetrating earth formations for, among other things, determining relative volumes of each one of a plurality of various fluids which may be entering the wellbore. An instrument which typically is included with production logging tools is a fluid density instrument. The fluid density instrument is used to make measurements related to the density, or specific gravity, of the fluids within the wellbore at a plurality of depths within the wellbore. Measurements of the density of the fluid filling the wellbore are typically combined with other measurements provided by the production logging tools to determine the relative volumes of each one of the plurality of fluids which may be present in the wellbore.

An instrument for measuring the density of the fluid in the wellbore is known in the art and is called a differential pressure fluid density (DPFD) instrument. A typical DPFD instrument is disclosed, for example, in U.S. Pat. No. 3,616,688 issued to Bonnet et al. The instrument in the Bonnet patent comprises a differential pressure transducer which is adapted to measure a difference in pressure between two spaced-apart locations along the tool. The difference in pressure measured by the transducer can be related to the density of the fluid disposed between the spaced-apart locations by the expression:

$$\rho = \frac{\Delta P}{g * \Delta V} \quad (1)$$

where $\rho$ is the density of the fluid, $\Delta P$ is the measured differential pressure, $g$ is the local acceleration due to gravity, and $\Delta V$ is the vertical separation of the spaced-apart locations between which the differential pressure is measured.

The distance between the spaced-apart locations along the tool known in the art typically represents a compromise between the sensitivity of the instrument, which generally increases as the distance increases, and the maximum differential pressure to which the transducer can be exposed without destructive failure, because for any given density of fluid disposed between the spaced-apart locations the differential pressure across the transducer typically increases as the distance between the spaced-apart locations increases.

A limitation of the DPFD instrument known in the art is that the sensitivity of the instrument is reduced when used in certain wellbores which may be inclined from vertical, because the magnitude of the differential pressure developed between the spaced-apart locations is related to the vertical separation between the spaced-apart locations, as previously explained herein. In highly inclined wellbores the vertical separation between the spaced-apart locations typically is very small. The actual vertical separation between the spaced-apart locations at any value of inclination from the vertical can be expressed as:

$$\Delta V = H * \cos(I) \quad (2)$$

where $\Delta V$ is the vertical separation between the spaced apart locations, $H$ is the distance between the spaced-apart locations, and $I$ is the angle of inclination of the wellbore from vertical (in a vertical wellbore $I=0$). It can be inferred from equation (2) that in wellbores approaching horizontal, the sensitivity of the DPFD tool known in the art is severely limited.

A further limitation of the DFPD instrument known in the art is that the sensitivity of the instrument can be reduced in fluids having densities nearly equal to the density of water, particularly fluids such as mixtures of crude oil and water having a large fractional composition of water, because small density differences generate differences in differential pressure across the transducer which may be below the resolution of the transducer.

It is an object of the present invention to provide a differential pressure fluid density instrument having a distance between spaced-apart locations which can be adjusted while the instrument is in the wellbore to compensate the measurement for use in inclined wellbores or for the presence of fluids in the wellbore having having particular densities which reduce the sensitivity of the tool.

SUMMARY OF THE INVENTION

The present invention is a differential pressure fluid density instrument comprising a housing having a plurality of ports at spaced-apart locations along the housing, a differential pressure transducer, and a valve adapted to selectively connect the transducer across two predetermined ones of the plurality of ports.

In a preferred embodiment of the invention, the valve comprises a three-way solenoid operated valve controllable by the system operator from the earth's surface.

DESCRIPTION OF THE PREFERRED EMBODIMENT

Figure 1:
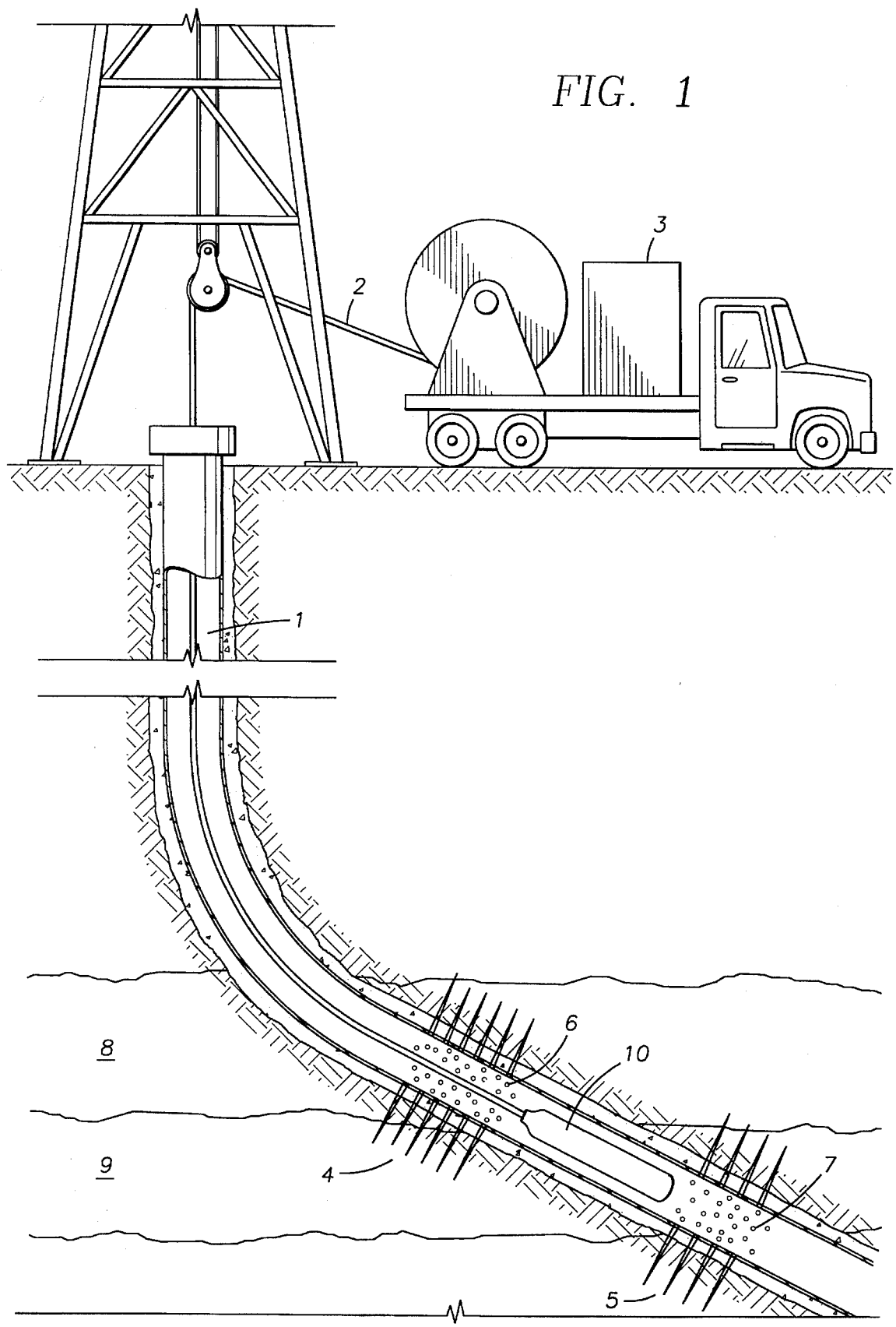
FIG. 1 shows a fluid density instrument according to the present invention disposed within a wellbore.

The operation of the present invention in a wellbore can be better understood by referring to FIG. 1. An electrical wireline or cable 2 comprising at least one insulated electrical conductor (not shown) is typically lowered into a wellbore 1 by means of a surface logging unit 3. A logging tool 10 comprising the fluid density instrument of the present invention is attached to the end of the cable 2 which is lowered into the wellbore 1. The logging unit 3 also comprises equipment (not shown separately) for sending electrical power to the tool 10 and receiving and interpreting signals transmitted up the cable 2 by the tool 10.

A first zone 4 completed in an upper earth formation 8, and a second zone 5 completed in a lower earth formation 9 are both in hydraulic communication with the wellbore 1. Hydraulic communication enables a first fluid 6 contained in the upper earth formation 8 and a second fluid 7 contained in the lower earth formation 9, which may have a different density than the first fluid 6, to flow into the wellbore 1. As the tool 10 is moved past the zones 4, 5 the tool 10 makes measurements corresponding to the relative volumes of the first 6 and second 7 fluids entering the wellbore 1 from the upper 8 and lower 9 earth formations, respectively.

Figure 2:
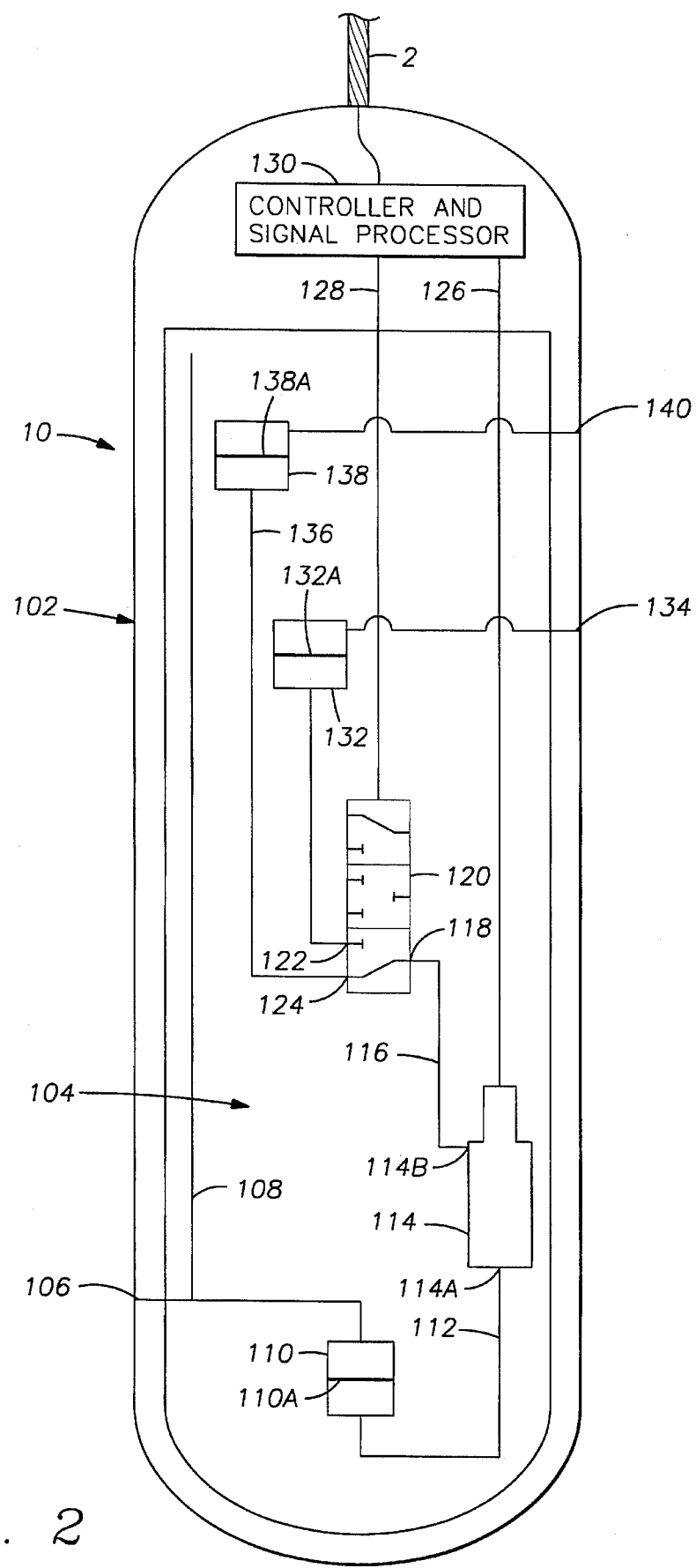
FIG. 2 shows the fluid density instrument of the present invention in detail.

The function of the present invention can be better understood by referring to FIG. 2. The tool 10 includes a housing 102 which can be attached at one end to the end of the cable 2. The housing 102 comprises an inner chamber 104 which can be filled with a liquid such as silicone oil. The liquid-filled chamber 104 is in hydraulic communication with the wellbore (shown as 1 in FIG. 1), which enables the housing 102 and components of the tool 10 disposed within the chamber 104, as will be further explained, to be constructed without the need to withstand high differential pressures. The chamber 104 includes a standpipe 108 which extends from near the bottom of the chamber 104 substantially to the top of the chamber 104. The standpipe 108 is also hydraulically connected to a lower port 106. The lower port 106 is in hydraulic communication with the wellbore 1. Fluids (shown as 6 and 7 in FIG. 1) in the wellbore 1 may enter the standpipe 108 through the lower port 106 as a result of thermal contraction or hydrostatic compression of the silicone oil in the chamber 104. The fluids 6, 7 which may enter the chamber 104 typically are less dense than the silicone oil and will therefore typically remain at the top of the chamber 104. When the silicone oil expands, the fluids 6, 7 will be expelled back through the standpipe 108 and thence back into the wellbore 1 through the lower port 106.

The lower port 106 is also in hydraulic communication with one end of a first expansion well 110. The first well 110 is included to reduce changes in the length of a column of silicone oil formed within the tool 10, as will be further explained. The first well 110 can be equipped with a separator cup 110A which is used to enable communication of changes in fluid pressure, while preventing the fluids 6, 7 entering the first well 110 via the lower port 106 from mixing with silicone oil disposed on the other side of the first cup 110A. The cup 110A can be composed of a polymeric material such as that sold under the trade name RYTON.

At its other end, the first well 110 is hydraulically connected by a lower signal line 112 to a first input 114A of a differential pressure transducer 114 disposed within the chamber 104. The lower signal line 112 can be formed, for example, from steel tubing having an internal diameter of 1/32 inch. The first well 110 typically is in the form of a cylinder having a length of 1/2 inch and an internal diameter of 1/4 inch. The first well 110 has an internal diameter eight times that of the lower line 112, and therefore has an internal volume per unit length 64 times that of the lower line 112. An interface between the fluids 6, 7 from the wellbore and silicone oil which fills the lower line 112 is disposed within the first well 110, usually positioned at the cup 110A. Changes in volume of the silicone oil within the lower signal line 112 caused by thermal expansion or hydrostatic compression will effect only very small changes in the length of the column of silicone oil column filling the lower line 112. The significance of the small change in length of the silicone oil column in the lower line 112 will be further explained.

A second input 114B of the transducer 114 is connected to one end of an intermediate signal line 116, which is also filled with silicone oil. The other end of the intermediate line 116 is connected to a common port 118 of a three-way valve 120 disposed within the chamber 104. The valve 120 in the present embodiment of the invention can be an electrically actuated solenoid valve. A first selective port 122 on the valve 120 is hydraulically connected to one end of an intermediate well 132. The intermediate well 132 can be similar in construction to, and serves the same purposes as the first well 110. The intermediate well 132 can also be equipped with a cup 132A similar to the cup 110A disposed within the first well 110. The other end of the intermediate well 132 is hydraulically connected to an intermediate port 134 which is positioned at a spaced-apart location along the housing 102 from the lower port 106. The intermediate port 134 is also in hydraulic communication with the wellbore 1.

When the valve 120 is selected to connect the common port 118 to the first selective port 122, the transducer 114 is hydraulically connected across the lower port and the intermediate port 134. The manner in which the valve 120 is operated, and the significance of connecting the transducer 114 across the ports 110, 134 will be further explained.

A second selective port 124 on the valve 120 is hydraulically connected to one end of an upper well 138 by an upper signal line 136 which is also filled with silicone oil. The upper well 138 is similar in construction to and serves a similar purpose to the lower well 110 and the intermediate well 132. The upper well 138 can be equipped with a cup 138A similar in construction and purpose to the cup 110A in the lower well 110. The other end of the upper well 138 is hydraulically connected to an upper port 140. The upper port 140 is positioned at a spaced-apart location further removed from the lower port 106 than is the intermediate port 134. The upper port 140 is also in hydraulic communication with the wellbore 1.

When the valve 120 is selected to connect the common port 118 to the second selective port 124, the transducer 114 is connected across the upper port 140 and the lower port 106, the significance of which will be further explained.

The valve 120 can be connected by an electrical control line 128 to a central processor 130 disposed within the housing 102. The processor 130 is adapted to receive signals transmitted by the logging unit (shown as 3 in FIG. 1) in response to commands entered by the system operator, or alternatively by commands automatically generated by a computer program resident in a computer (not shown separately) forming part of the logging unit 3. The signals received by the processor 130 are converted therein into a control current conducted to the valve 120 by the control line 128. The control current actuates the valve 120 to connect the common port 118 to either the first 122 or second 124 selective port.

The transducer 114 generates an electrical signal in response to a difference in pressure between pressures applied to the inputs 114A and 114B. The electrical signal from the transducer 114 is connected to the processor 130 by an electrical signal line 126. The signal is conditioned in the processor 130 and sent to the logging unit 3 for decoding and interpretation.

The differential pressure which is present across the inputs 114A, 114B of the transducer 114 at any instant is related to: the difference in density between the fluids 6, 7 in the wellbore present between the lower port 106, and either the intermediate port 134 or the upper port 140, depending on which of the ports is connected by the valve 120; and the density of the silicone oil filling the lower signal line 112, the intermediate signal line 116 and the upper signal line 136. The density of the silicone oil is typically known, since it can be precisely measured before insertion into the tool 10. The differential pressure across the transducer 114 is also related to the vertical separation between the ports 106, and 134 or 140 which are connected across the transducer 114, and the vertical height of the slilcone oil column. The wells 110, 132, 138, as previously described herein, maintain a substantially constant level of the fluid interface between the silicone oil and fluids 6, 7 from the wellbore 1 inside the wells 110, 132, 138, so that the length of the silicone oil column is accurately known.

In an instance where the fluids 6, 7 filling the wellbore 1 are only slightly different in density than the silicone oil, for example in mixtures of crude oil and water having a very high fraction of water, the valve 120 can be selected by the system operator to connect the transducer 114 to the upper port 140. Selecting the upper port 140 increases the effective distance between the spaced-apart locations, thereby increasing a differential pressure developed across the transducer 114 for any particular difference in density between the silicone oil and the fluids 6, 7 in the wellbore 1, as can be inferred by referring to equation (1). The larger differential pressure developed across the transducer 114 will increase the ability of the tool 10 to resolve small differences in density of the fluids 6, 7 in the wellbore 1.

The valve 120 can also be operated to select the upper port 140, for example where the wellbore 1 is highly inclined from vertical, whereby the effective vertical distance between the spaced-apart locations of the ports 106, 134, 140 is small. By selecting the upper port 140, the differential pressure applied across the transducer 114 can be increased for any particular density of fluids 6, 7 in the wellbore 1, thereby increasing the sensitivity of the tool 10.

The valve 120 can be operated to select the intermediate port 134 in instances where the wellbore 1 is filled with fluids having widely different densities, such as mixtures of oil, gas and water. In these instances it can be desirable to have the tool 10 able to measure a wide range of densities. By selecting the intermediate port 134, the differential pressure developed across the transducer 114 for any particular value of density of the fluids 6, 7 in the wellbore 1 is reduced, reducing the sensitivity of the tool 10. Reducing the sensitivity of the tool 10 can increase the useful measurement range.

It is to be understood that other configurations of valves, ports and transducers can be used to achieve the same result as that of the present embodiment of the invention, and the present embodiment of the invention should be used only for purposes of illustration. The invention should be limited in scope only by the claims appended hereto.

What is claimed is:

1. A differential pressure fluid density instrument comprising:

a housing adapted to traverse a wellbore penetrating an earth formation, said housing including a plurality of ports positioned at spaced-apart locations along said housing;

a differential pressure transducer disposed within said housing;

a valve, disposed within said housing and adapted to selectively connect said transducer across two predetermined ones of said plurality of ports; and a fluid expansion well connected at one end to one of said ports, said fluid expansion well at least partially filled with a fluid of known density.

2. The fluid density instrument according to claim 1 wherein said valve comprises a three-way solenoid operated valve.

3. The fluid density instrument according to claim 1 wherein said housing further comprises an inner chamber filled with a liquid and having a standpipe, said standpipe at one end in hydraulic communication with one of said plurality of ports, said standpipe extending substantially to the top of said chamber so that fluids entering said chamber from said wellbore are expelled by expansion of said liquid.

4. A differential pressure fluid density, instrument comprising:

a housing adapted to traverse a wellbore penetrating an earth formation, said housing including a plurality of ports positioned at spaced-apart locations along said housing;

a differential pressure transducer disposed within said housing;

a valve, disposed within said housing and adapted to selectively connect said transducer across two predetermined ones of said plurality of ports; and an inner chamber filled with a liquid and having a standpipe, said standpipe at one end in hydraulic communication with one of said plurality of ports, said standpipe extending substantially to the top of said chamber so that fluids entering said chamber from said wellbore are expelled by expansion of said liquid.

5. The fluid density instrument according to claim 4 wherein said valve comprises a three-way solenoid operated valve.

* * * * *